United States Patent
Bacher et al.

(10) Patent No.: US 10,194,999 B2
(45) Date of Patent: Feb. 5, 2019

(54) MEDICAL INSTRUMENT HAVING A SHAFT WITH A FLEXIBLE PORTION AND WITH A CONTROLLED CURVABLE PORTION

(71) Applicant: Karl Storz SE & Co. KG, Tuttlingen (DE)

(72) Inventors: Uwe Bacher, Tuttlingen (DE); Sabine Zahler, Vaterstetten (DE); Martin Leonhard, Emmingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 1024 days.

(21) Appl. No.: 13/900,171

(22) Filed: May 22, 2013

(65) Prior Publication Data

US 2013/0338647 A1    Dec. 19, 2013

(30) Foreign Application Priority Data

May 23, 2012  (DE) ........................ 10 2012 208 605

(51) Int. Cl.
| | |
|---|---|
| *A61N 5/00* | (2006.01) |
| *A61B 17/29* | (2006.01) |
| *A61B 90/50* | (2016.01) |
| *A61B 17/00* | (2006.01) |

(52) U.S. Cl.
CPC .............. *A61B 90/50* (2016.02); *A61B 17/29* (2013.01); *A61B 17/2909* (2013.01); *A61N 5/00* (2013.01); *A61B 2017/003* (2013.01); *A61B 2017/0046* (2013.01); *A61B 2017/2905* (2013.01)

(58) Field of Classification Search
CPC ..... A61B 17/29; A61B 17/2909; A61B 17/30; A61B 17/1608; A61B 2017/003; A61B 2017/00424; A61B 2017/0046; A61B 2017/292; A61B 2017/2927; A61B 2017/2905; A61B 2017/2929; A61B 2017/2939; A61B 2017/291
USPC ........... 600/1, 131, 139, 141, 146, 149, 205; 606/130
See application file for complete search history.

(56) References Cited

U.S. PATENT DOCUMENTS

| | | | |
|---|---|---|---|
| 6,569,105 B1 * | 5/2003 | Kortenbach | A61B 10/06 600/562 |
| 8,518,024 B2 * | 8/2013 | Williams | A61B 1/00052 606/1 |
| 2006/0199999 A1 * | 9/2006 | Ikeda | A61B 1/0052 600/141 |
| 2008/0188868 A1 | 8/2008 | Weitzner et al. | |
| 2009/0054733 A1 | 2/2009 | Marescaux et al. | |
| 2009/0069842 A1 | 3/2009 | Lee et al. | |
| 2009/0247994 A1 | 10/2009 | Bacher et al. | |
| 2009/0299344 A1 * | 12/2009 | Lee | A61B 17/062 606/1 |
| 2010/0030029 A1 | 2/2010 | Markham | |

(Continued)

FOREIGN PATENT DOCUMENTS

| | | |
|---|---|---|
| DE | 69403583 T2 | 10/1997 |
| EP | 2027820 A1 | 2/2009 |
| WO | 2012106187 A1 | 8/2012 |

*Primary Examiner* — John P Leubecker
*Assistant Examiner* — William Chou
(74) *Attorney, Agent, or Firm* — Whitmyer IP Group LLC (57) ABSTRACT

A shaft for a medical instrument includes a controlled curvable portion or a hinge, an uncontrolled flexible portion, and a shaft coupling device for the releasable mechanical connection of the shaft to a maneuvering device.

21 Claims, 4 Drawing Sheets

(56) References Cited

U.S. PATENT DOCUMENTS

| | | |
|---|---|---|
| 2010/0286480 A1 | 11/2010 | Peine |
| 2011/0295242 A1* | 12/2011 | Spivey ............. A61B 17/07207 606/1 |
| 2012/0095298 A1* | 4/2012 | Stefanchik ......... A61B 17/2909 600/219 |
| 2012/0143206 A1* | 6/2012 | Wallace ........... A61B 17/00234 606/103 |
| 2013/0138136 A1* | 5/2013 | Beckham ......... A61B 17/12113 606/200 |

* cited by examiner

MEDICAL INSTRUMENT HAVING A SHAFT WITH A FLEXIBLE PORTION AND WITH A CONTROLLED CURVABLE PORTION

FIELD OF THE INVENTION

The present invention relates to a medical instrument having a shaft with an uncontrolled flexible portion and a controlled curvable portion.

BACKGROUND OF THE INVENTION microinvasive surgery, particularly in intraluminal and transluminal microinvasive surgery, medical instruments with long, thin, flexible shafts are used, which can be introduced into the esophagus, stomach and intestine. The distal end of the flexible shaft is curvable in a controlled manner, for example in order to be able to position a cutting or grasping tool in any desired way inside a cavity.

SUMMARY OF THE INVENTION

It is an object of the present invention to make available an improved medical instrument having a shaft with a curvable portion and an uncontrolled flexible portion, a shaft with a controlled curvable portion and an uncontrolled flexible portion, and a maneuvering device for a medical instrument.

This object is achieved by the subjects of the independent claims.

Developments are set forth in the dependent claims.

A shaft for a medical instrument comprises a tool or a coupling for a tool, a controlled curvable portion or a hinge, an uncontrolled flexible portion, and a shaft coupling device for the releasable mechanical connection of the shaft to a maneuvering device.

The controlled curvable portion has a controllable curvature. The curvature of the flexible portion is not controllable. The controlled curvable portion or the hinge is in particular arranged on or near the distal end of the shaft. The curvature of the controlled curvable portion, or the angle position of the hinge, is in particular controllable by means of a maneuvering device, which is mechanically connected to the shaft coupling device. The uncontrolled flexible portion of the shaft is in particular arranged in the proximal direction from the controlled curvable portion or hinge and extends along a large part of the total length of the shaft. The shaft and its properties and features are provided and designed in particular for use in intraluminal and transluminal microinvasive surgery.

A portion of the shaft is flexible if it is reversibly curvable at least as far as a maximum curvature or a minimum radius of curvature and in particular is completely elastically or at least partially elastically curvable. The elastic properties of the uncontrolled flexible portion, its maximum curvature and its minimum radius of curvature are adapted to the intended use of the shaft, in particular to the properties of the hollow organ in which the shaft is to be inserted.

The shaft coupling device is arranged in particular at the proximal end of the shaft or forms the proximal end of the shaft. The shaft coupling device is designed in particular for the rigid mechanical connection of the proximal end of the shaft to a maneuvering device.

The shaft coupling on the shaft permits repeated, non-destructive separation and subsequent mechanical connection of the shaft and a maneuvering device. Therefore, for example, a damaged shaft can be replaced or repaired while the maneuvering device continues to be used. Correspondingly, a damaged maneuvering device can be replaced or repaired while the shaft continues to be used. Moreover, different shafts for different uses and/or with different lengths, cross sections or other properties can be combined with the same maneuvering device. Moreover, different maneuvering devices can be combined with one shaft, for example for left-handed or right-handed use or for different hand sizes of the medical personnel guiding the maneuvering device. Moreover, both shaft and maneuvering device can be further developed independently of each other. Therefore, a medical establishment can profit from the further developments by re-purchasing only the further developed shaft or only the further developed maneuvering device and continuing to use the respective other component available from its stock.

The modular nature of the medical instrument composed of shaft and maneuvering device thus permits, among other things, a more versatile use or an adaptation to a greater variety of uses and/or the stocking of a smaller number of shafts and maneuvering devices, with correspondingly lower investment costs and with correspondingly less logistical demand.

A shaft, as it is described here, also comprises in particular a transmission device for transmitting at least either a force or a torque between the proximal end of the shaft and the controlled curvable portion or the hinge.

The transmission device is designed in particular for the mechanical transmission of a push force and/or tensile force and/or torque. So as not to impair the flexibility of the uncontrolled flexible portion arranged in particular in the proximal direction from the controlled curvable portion, the transmission device itself is also flexible. The transmission device extends from the proximal end of the shaft as far as the controlled curvable portion or the hinge.

In a shaft with a transmission device, as it is described here, the transmission device comprises in particular a pull cable or a pull wire.

The transmission device can comprise two, three, four or more pull cables or pull wires, which are arranged alongside one another and which each extend from the proximal end of the shaft as far as the controlled curvable portion of the shaft. The one or more pull cables are in particular each suitable exclusively for the transmission of tensile forces. Alternatively or in addition, the transmission device can comprise one or more components designed for the transmission of push/thrust forces, or both for the transmission of tensile forces and also for the transmission of push/thrust forces.

A pull cable or a pull wire can be designed with a relatively small cross section, and therefore also with relatively great mechanical flexibility, for the transmission of a substantial tensile force. By means of one pull cable or one pull wire, it is possible to control the curvature of the controlled curvable portion or the angle of the hinge in one plane. For example, a spring or another elastic element restores the controlled curvable portion or the hinge to a predetermined position when the proximal end of the pull cable or of the pull wire is freed. With two, three or more pull cables or pull wires, restoring is possible even without an elastic element and/or a curvature of the controlled curvable portion or an angled arrangement of the hinge is possible in two mutually perpendicular directions. A curvature of the controlled curvable portion or an angled arrangement of the hinge in two mutually perpendicular directions has the effect that the distal end of the shaft can be moved not only on an arc (in the case of the hinge: an arc of a circle)

but also on a section of a dome-shaped curved surface (in the case of the hinge: in particular a spherical surface).

A shaft with a transmission device, as it is described here, also comprises in particular a transmission coupling device at the proximal end of the shaft, for releasable mechanical coupling to a corresponding transmission coupling device on a maneuvering device.

By means of the transmission coupling device on the shaft and a corresponding transmission coupling device on a maneuvering device, the transmission device of the shaft and an actuating device on the maneuvering device can be mechanically coupled. In this way, the curvature of the controlled curvable portion or the angle of the hinge can be controlled by manual actuation of the actuating device on the maneuvering device.

In a shaft with a transmission coupling device, as it is described here, the transmission coupling device is designed in particular for a latching connection to a corresponding transmission coupling device on a maneuvering device.

For a latching connection, the transmission coupling device has in particular an elastic portion and/or a ramp-shaped portion. The latching connection permits an automatic or straightforward form-fit, mechanical connection of the transmission coupling device to a corresponding transmission coupling device of a maneuvering device. The combination of a shaft and of a maneuvering device to form a medical instrument can in this way be simplified and medical personnel assisted.

In a shaft with a transmission coupling device, as it is described here, the transmission coupling device has, at its proximal end, a concave portion.

The concave portion has in particular a shape that corresponds to a convex portion of a corresponding transmission coupling device on a maneuvering device. A concave portion is a portion with a depression or a recess. A convex portion is a protruding or salient portion. In particular, the concave portion is designed to receive a spherical portion on a corresponding transmission coupling device.

Alternatively, in a shaft with a transmission coupling device, as it is described here, the transmission coupling device has, at its proximal end, a convex portion. The convex portion has in particular a shape corresponding to a concave portion of a corresponding transmission coupling device on a maneuvering device. In particular, the convex portion has an area in the form of a spherical surface.

In a shaft with a transmission coupling device, as it is described here, the shaft coupling device and the transmission coupling device are in particular arranged and designed in such a way that a mechanical connection between the shaft coupling device and a corresponding coupling device on a maneuvering device and a mechanical coupling of the transmission coupling device to a corresponding transmission coupling device on the maneuvering device can be released by means of a rotation of the shaft relative to the maneuvering device.

In particular, the rigid mechanical connection of the shaft coupling device of the shaft to the corresponding coupling device of the maneuvering device (and therefore the rigid mechanical connection of the proximal end of the shaft to the maneuvering device) and the mechanical coupling of the transmission coupling device of the shaft to the corresponding transmission coupling device of the maneuvering device (and therefore the mechanical coupling of the transmission device of the shaft to an associated actuating device of the maneuvering device) can be released by means of a rotation of the shaft about the longitudinal axis of the proximal end of the shaft. The mechanical connection between the shaft coupling device of the shaft and the corresponding coupling device of the maneuvering device and the mechanical coupling of the transmission coupling device of the shaft to the corresponding transmission coupling device of the maneuvering device are released at the same time, or substantially at the same time, or in succession, by a relative rotation through a predetermined angle.

Being able, with a single rotation movement of the shaft relative to the maneuvering device, to release both the mechanical connection between the shaft coupling device of the shaft and the corresponding coupling device of the maneuvering device, and also the mechanical coupling of the transmission coupling device to the corresponding transmission coupling device of the maneuvering device, permits simplified handling when disassembling a medical instrument into the shaft and the maneuvering device. This reduces the time needed for disassembly and reduces the risk of damage resulting from an error during disassembly.

A shaft, as it is described here, in particular comprises several transmission coupling devices. Each individual transmission coupling device has in particular the above-described features. In particular, each individual transmission coupling device is provided and arranged corresponding to, and for coupling to, a transmission coupling device of a maneuvering device.

In a shaft, as it is described here, several transmission coupling devices for controlling the controlled curvable portion are in particular provided at the proximal end of the shaft.

The transmission coupling devices are in particular identical or correspond to one another in terms of their shape and their other properties. Each transmission coupling device is in particular connected to an associated pull cable or an associated pull wire.

A shaft, as it is described here, also comprises in particular a further transmission device for transmitting at least either a force or a torque between the proximal end of the shaft and a tool at the distal end of the shaft, and a further transmission coupling device for the mechanical coupling of the transmission device to a corresponding transmission coupling device on a maneuvering device, wherein the further transmission device is arranged outside the shaft coupling device.

In particular, the further transmission device is arranged outside the shaft coupling device and at a distance from the shaft coupling device. This arrangement of the further transmission coupling device can allow separate manual coupling and uncoupling of the further transmission device and of a further actuating device, on a maneuvering device, corresponding to the further transmission coupling device.

A maneuvering device for a medical instrument comprises a shaft coupling device for the releasable mechanical connection of the maneuvering device to a shaft with a controlled curvable portion or a hinge and with an uncontrolled flexible portion, a first actuating device for controlling a tool at the distal end of the shaft, a second actuating device for manually controlling the curvature of the controlled curvable portion or hinge of the shaft, and a transmission coupling device for the releasable mechanical coupling of the second actuating device to a transmission device for transmitting at least either a force or a torque to the controlled curvable portion or hinge of the shaft.

The maneuvering device is provided in particular to form a medical instrument together with a shaft, as it is described here. The shaft coupling device is in particular formed at the distal end of the maneuvering device and in particular designed for releasable rigid mechanical connection of the maneuvering device to the proximal end of the shaft. The transmission coupling device is in particular likewise arranged at the distal end of the maneuvering device.

In a maneuvering device, as it is described here, the transmission coupling device is designed in particular for a latching connection to a corresponding transmission coupling device on a shaft connected to the maneuvering device.

For this purpose, the transmission coupling device of the maneuvering device has in particular an elastic portion and/or a ramp-shaped portion.

In a maneuvering device, as it is described here, the transmission coupling device has in particular, at its distal end, a convex portion.

The convex portion has in particular a shape corresponding to a concave portion of a transmission coupling device on a shaft connected to the maneuvering device. In particular, the convex portion has spherical surface areas.

Alternatively, in a maneuvering device, as it is described here, the transmission coupling device has in particular, at its proximal end, a concave portion. The concave portion has in particular a shape corresponding to a convex portion of a transmission coupling device on a flexible shaft connected to the maneuvering device.

In a maneuvering device, as it is described here, the second actuating device is in particular rotatable or pivotable about an axis, wherein the transmission coupling device is mechanically coupled to the second actuating device by means of a connector rod. The axis about which the second actuating device is rotatable or pivotable is in particular perpendicular to the longitudinal axis of the proximal end of a shaft connected mechanically to the maneuvering device.

In a maneuvering device, as it is described here, the shaft coupling device and the transmission coupling device are in particular arranged and designed in such a way that a mechanical connection between the shaft coupling device and a corresponding coupling device on a shaft and a mechanical coupling of the transmission coupling device to a corresponding transmission coupling device on the shaft can be released by means of a rotation of the maneuvering device relative to the shaft.

In a shaft, as it is described here, and in a maneuvering device, as it is described here, the shaft coupling devices are designed in particular as bayonet couplings. A locking device can be provided for locking the coupling device. Such a locking device can comprise a bolt, which is movable parallel or substantially parallel to the longitudinal axis of the proximal end of the shaft.

A maneuvering device, as it is described here, comprises in particular several transmission coupling devices, wherein each transmission coupling device can have the properties of a transmission coupling device that are described here.

In a shaft, as it is described here, or in a maneuvering device, as it is described here, several transmission coupling devices are in particular arranged symmetrically with respect to the longitudinal axis of the shaft.

In the maneuvering device, as it is described here, the transmission coupling devices are in particular arranged symmetrically with respect to the longitudinal axis of a proximal end of a shaft connected mechanically to the maneuvering device.

A symmetrical arrangement of several transmission coupling devices with respect to an axis of symmetry is present when the locations and the orientations of the transmission coupling devices emerge from one another or are brought into one another by rotation through an integral fraction of 360° about the axis of symmetry.

A medical instrument comprises a shaft, as it is described here, and a maneuvering device, as it is described here.

Properties, features and advantages of the maneuvering device and of the medical instrument correspond substantially or completely to those described above for the shaft.

BRIEF DESCRIPTION OF THE DRAWINGS

Embodiments are explained in more detail below with reference to the attached figures, in which.

DETAILED DESCRIPTION OF THE INVENTION

Figure 1:
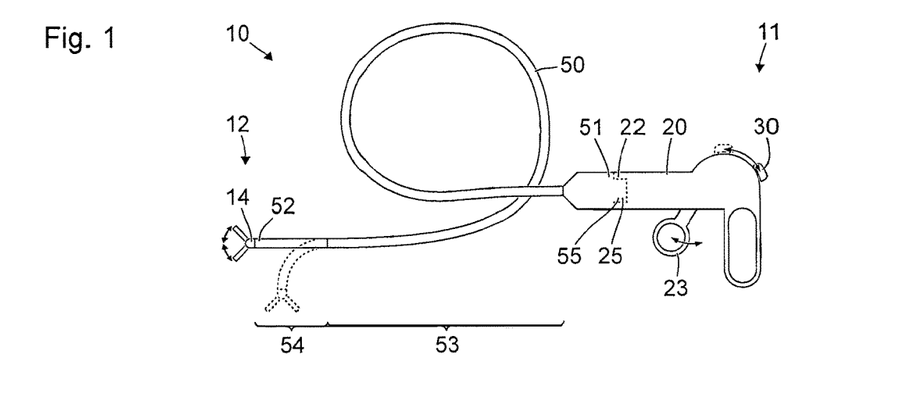
FIG. 1 shows a schematic view of a medical instrument.

FIG. 1 shows a schematic view of a medical instrument 10 with a proximal end 11 and a distal end 12. The medical instrument 10 is provided and designed in particular for use in microinvasive surgical interventions or in other microinvasive diagnostic, therapeutic and/or surgical procedures. The medical instrument 10 has, at the distal end 12, a tool 14, which is indicated in FIG. 1 by way of example as a grasping or cutting tool with two pivotable jaw parts. At the proximal end 11, the medical instrument 10 has a maneuvering device 20. The distal end 22 of the maneuvering device 20 is connected to the tool 14 by a shaft 50.

The maneuvering device 20 comprises a movable, in particular pivotable, grip part 23 which, by means of a transmission device (not shown in FIG. 1) in the shaft 50, is mechanically coupled to the jaw parts of the tool 14. The pivotable grip part 23 is an actuating device for the tool 14. Arrows on the movable grip part 23 and on the jaw parts of the tool 14 indicate that a movement of the movable grip part 23 is accompanied by a movement of the jaw parts of the tool 14.

The proximal end 51 of the shaft 50 is connected mechanically to the maneuvering device 20 in a rigid but releasable manner. In particular, a convex area 55 at the proximal end 51 of the shaft 50 engages in a recess 25 at the distal end 22 of the maneuvering device 20. Examples of details of the rigid and releasable mechanical connection of the distal end 22 of the maneuvering device 20 to the proximal end 51 of the shaft 50 are described below with reference to FIGS. 4 to 6. The distal end 52 of the shaft 50 is mechanically connected to the tool 14 in a permanent manner, i.e. not releasable without destruction, or alternatively in a manner releasable without destruction.

The shaft 50 has an uncontrolled flexible portion 53 and a controlled curvable portion 54. The properties of the uncontrolled flexible portion 53 of the shaft 50, in particular its elastic (and optionally to a lesser extent also plastic) properties, the minimum attainable radius of curvature, its cross section and its surface qualities, are adapted to the intended use of the medical instrument 10, for example in order to permit insertion into the esophagus, the stomach or the intestine of a patient.

The controlled curvable portion 54 of the shaft 50 is mechanically coupled to an actuating device 30 on the maneuvering device 20 by way of a further transmission device (likewise not shown in FIG. 1) in the interior of the shaft 50. In FIG. 1, the actuating device 30 is shown in two different positions indicated by solid lines and broken lines, and the controlled curvable portion 54 of the shaft 50 is shown in two different spatial configurations or with two different curvatures. The two positions of the actuating device 30 that are shown in FIG. 1, and the two curvatures of the controlled curvable portion 54 of the shaft 50 that are shown in FIG. 1, are for example two extreme positions or two extreme states of curvature, respectively. In particular, the position of the actuating device 30 indicated by the solid line and the state of curvature of the controlled curvable portion 54 indicated by the solid line correspond to each other. In particular, the position of the actuating device 30 indicated by the broken line and the state of curvature of the controlled curvable portion 54 of the shaft 50 indicated by the broken line correspond to each other. By manual activation of the actuating device 30, or by manual movement of the actuating device 30 on the maneuvering device 20, medical personnel can vary and set the state of curvature of the controlled curvable portion 54.

Figure 2:
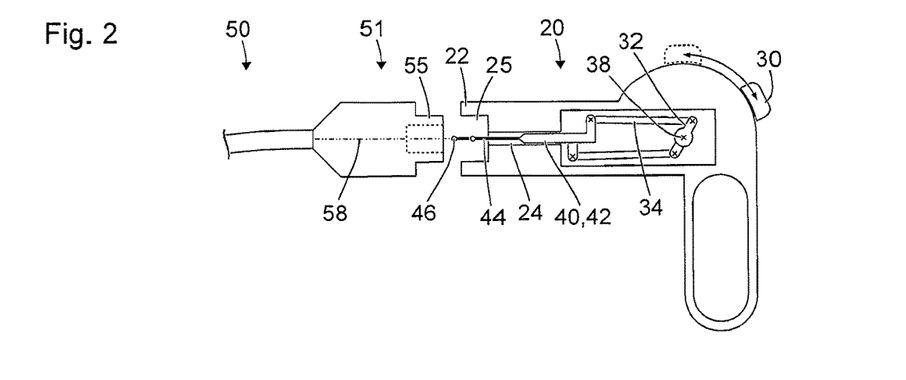
FIG. 2 shows a further schematic view of part of the medical instrument from FIG. 1.

FIG. 2 shows an enlarged schematic view of the maneuvering device 20 and of the proximal end 51 of the shaft 50 from FIG. 1. The maneuvering device 20 is depicted partially in cross section in FIG. 2 in order to show devices and features provided in the interior of the maneuvering device 20.

The actuating device 30 is mechanically coupled to a crank 32 in such a way that a manual movement of the actuating device 30 is accompanied by a pivoting of the crank 32 about its pivot axis 38. In particular, the actuating device 30 is movable along an arc of a circle, of which the center point lies on the pivot axis 38, and is connected rigidly to the crank 32.

Transmission coupling devices 40 are arranged in two respective guide channels 24 in the maneuvering device 20. One of the two guide channels 24 is opened in cross section in FIG. 2, while the second guide channel in the illustrated example lies concealed behind the drawing plane. The guide channels 24 and the transmission coupling devices 40 are designed in such a way that the transmission coupling devices 40 are linearly movable in the guide channels 24 in a predetermined direction and are guided with minimal play and minimal friction in both directions perpendicular to the predetermined direction.

A transmission coupling device 40 in each case has a portion 42 which is guided in the guide channel 24, and of which the cross section is adapted to the cross section of the guide channel. The proximal end of each transmission coupling device 40 is connected in an articulated manner to one end of the crank 32 via an associated connector rod 34. In the example shown, the two ends of the crank 32, which are each connected by a respective connector rod 34 to a proximal end of a transmission coupling device 40, are spaced apart from the pivot axis 38 in opposite directions relative to the pivot axis 38 of the crank 32. By means of the (in particular rigid) coupling of the actuating device 30 to the crank 32, and by way of the connector rods 34, a movement of the actuating device 30 is accompanied by linear movements of the transmission coupling devices 40 in two opposite directions.

In the distal direction from the portion 42 guided in the guide channel 24, each transmission coupling device 40 has an elastic portion 44 and, at the distal end of the elastic portion 44, a ball 46. The elasticity of the elastic portions 44 of the transmission coupling devices 40 results in particular from their much reduced cross section in relation to the portion 42 guided in the guide channel 24. The cross sections of the elastic portions 44 of the transmission coupling devices 40 are, for example, circular, square or rectangular with long sides in the direction perpendicular to the drawing plane of FIG. 2. The elasticity of the elastic portions 44 of the transmission coupling devices 40 allows the balls 46 at the distal ends of the elastic portions 44 to deflect from the rest positions shown in FIG. 2. This deflection is explained below with reference to FIG. 12.

The proximal end 51 of the shaft 50 has a longitudinal axis 58. The convex area 55 at the proximal end 51 of the shaft 50 is substantially rotationally symmetrical with respect to the longitudinal axis 58, particularly having the shape of a circular cylinder in part. The recess 25 at the distal end 22 of the maneuvering device 20 is likewise substantially rotationally symmetrical with respect to the longitudinal axis 58 of the proximal end 51 of the flexible shaft 50 when the proximal end 51 is oriented relative to the maneuvering device 20 in the manner shown in FIG. 2.

Proceeding from the arrangement and orientation of the proximal end 51 of the shaft 50 relative to the distal end 22 of the maneuvering device 20 as shown in FIG. 2, both can be joined together. For this purpose, the proximal end 51 of the shaft 50 is moved parallel to the longitudinal axis 58 onto the distal end 22 of the maneuvering device 20, and the convex area 55 is inserted into the recess 25, as is indicated in FIG. 1. The cross sections of the recess 25 at the distal end 22 of the maneuvering device 20 and of the convex area 55 at the proximal end 51 of the shaft 50 are adapted to each other in such a way that, in the configuration shown in FIG. 1, the convex area 55 at the proximal end 51 of the shaft 50 is guided with minimal play in the recess 25 at the distal end 22 of the maneuvering device 20. Form-fit engagement between the convex area 55 and the recess 25 fixes the orientation of the proximal end 51 of the shaft 50 relative to the distal end 22 of the maneuvering device 20. By means of a subsequent rotation movement of the proximal end 51 of the shaft 50 relative to the distal end 22 of the maneuvering device 20, a tension-resistant connection between both can be produced in the manner of a bayonet connection.

In the intended orientation of the proximal end 51 of the shaft 50 relative to the distal end 22 of the maneuvering device 20 as shown in FIG. 2, the directions which are predetermined by the guide channels 24, and in which the transmission coupling devices 40 are movable, are arranged parallel to the longitudinal axis 58. In particular, the transmission coupling devices 40 are arranged symmetrically with respect to the longitudinal axis 58, i.e. the positions and orientations of the transmission coupling devices 40 are 180 degrees from one another by rotation about the longitudinal axis 58.

Figure 3:
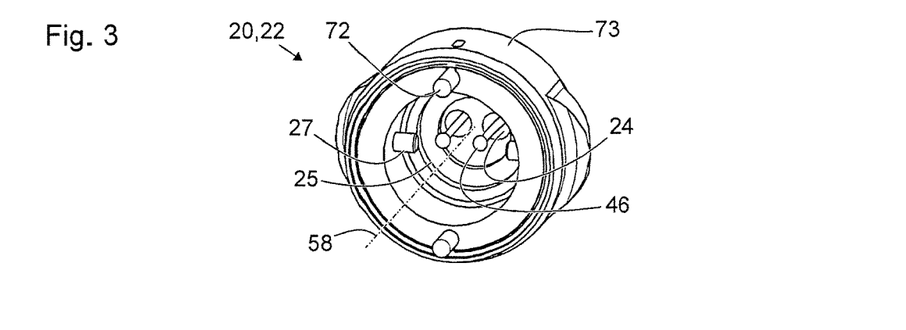
FIG. 3 shows a schematic axonometric view of a distal end of a maneuvering device.

FIG. 3 shows a schematic axonometric view of the distal end 22 of a maneuvering device 20 which, in terms of some features and properties, is similar to the maneuvering device from FIGS. 1 and 2. The following description deals mainly with the features and properties which the maneuvering device discussed with reference to FIGS. 1 and 2 does not have, or which are not shown in FIGS. 1 and 2.

Two bayonet lugs or catches 27 are arranged at mutually opposite locations in the recess 25. The catches 27 are, in particular, circular cylindrical pins fitted in bores in the wall surrounding the recess 25.

Two substantially pin-shaped bolts 72 are arranged on two mutually opposite sides of the edge of the recess 25. A ring 73 is rigidly connected to the two bolts 72. The ring 73, together with the bolts 72, is movable relative to the distal end 22 of the maneuvering device 20 in a direction parallel to the longitudinal axis 58. One or more springs (not shown in FIG. 3) or other elastic elements hold the ring 73 and the bolts 72 in the distal position shown in FIG. 3. The ring 73, together with the bolts 72, can be moved manually in the proximal direction counter to the force of the springs or other elastic elements.

Figure 4:
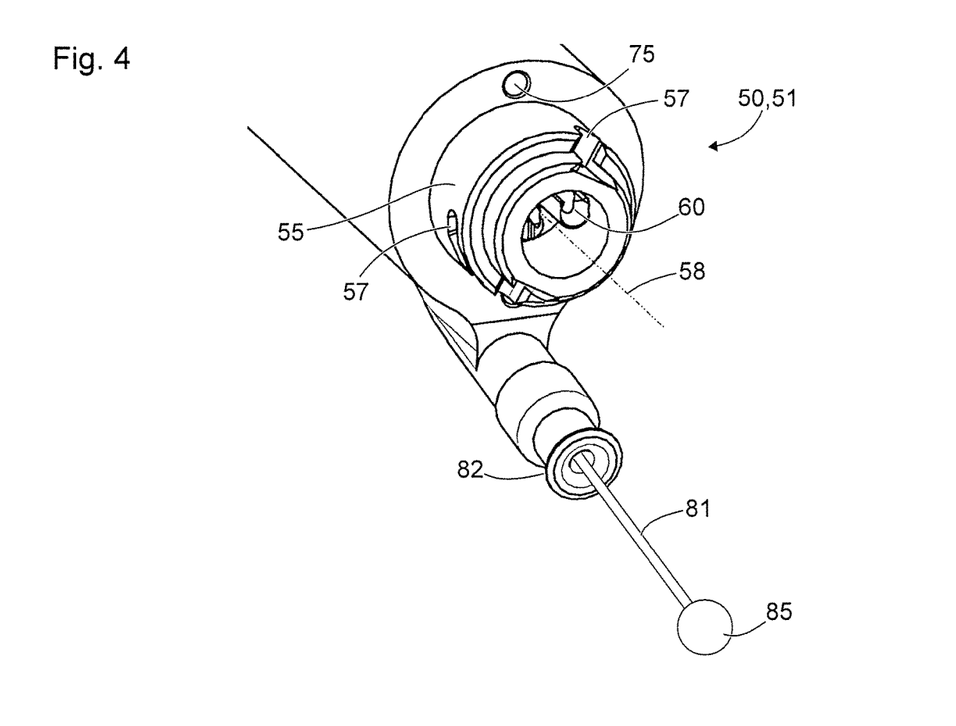
FIG. 4 shows a schematic axonometric view of a proximal end of a shaft.

FIG. 4 shows a schematic axonometric view of the proximal end 51 of a shaft 50 which, in terms of some features and properties, is similar to the shaft from FIGS. 1 and 2. The following description deals mainly with the features and properties which the shaft discussed with reference to FIGS. 1 and 2 does not have, or which are not shown in FIGS. 1 and 2.

In a recess in the convex area 55 of the proximal end 51 of the shaft 50, the proximal ends of two transmission coupling devices 60 can be seen which, along with their function, are discussed in more detail below with reference to FIGS. 7 to 12. On the outer circumference of the convex area 55, two L-shaped grooves 57 are provided, which are arranged lying opposite each other. Each L-shaped groove 57 has a portion parallel to the longitudinal axis 58 of the proximal end 51 of the shaft 50, and a further portion which extends substantially in the circumferential direction. The arrangement and configuration of the catches 27 shown at the distal end 22 of the maneuvering device 20 in FIG. 3, on the one hand, and of the L-shaped grooves 57 at the proximal end 51 of the shaft 50, on the other hand, are adapted to one another such that the catches 27 can be moved in the L-shaped grooves 57.

Moreover, two recesses 75 are provided at the proximal end 51 of the shaft 50 and lie opposite each other with respect to the longitudinal axis 58 of the proximal end 51 of the shaft 50. The arrangement and the cross sections of the recesses 75 at the proximal end 51 of the shaft 50 are adapted to the arrangement and the cross sections of the bolts 72 at the distal end 22 of the maneuvering device 20, such that the bolts 72 at the distal end 22 of the maneuvering device 20 can engage in the recesses 75 at the proximal end 51 of the shaft 50 when the catches 27 (cf. FIG. 3) are arranged in those ends of the circumferential portions of the L-shaped grooves 57 directed away from the axial portions.

Moreover, a nozzle 82 is arranged at the proximal end 51 of the shaft 50, through which nozzle 82 a transmission device 81 in the form of a wire or cable emerges from the proximal end 51 of the shaft 50. At its proximal end, the transmission device 81 has a transmission coupling device 85 (indicated only schematically in FIG. 4) for indirect or direct mechanical coupling of the transmission device 81 to an actuating device on a maneuvering device. In particular, the transmission coupling device 85 is provided for mechanical coupling to a grip part 23 (cf. FIG. 1) on a maneuvering device, which grip part 23 is pivotable or is movable along a path. The transmission device 81 then couples the grip part 23 to a tool 14 at the distal end 52 of the shaft 50 (cf. FIG. 1) in such a way that a movement of the grip part 23 is accompanied, for example, by a movement of jaw parts of the tool 14.

Figure 5:
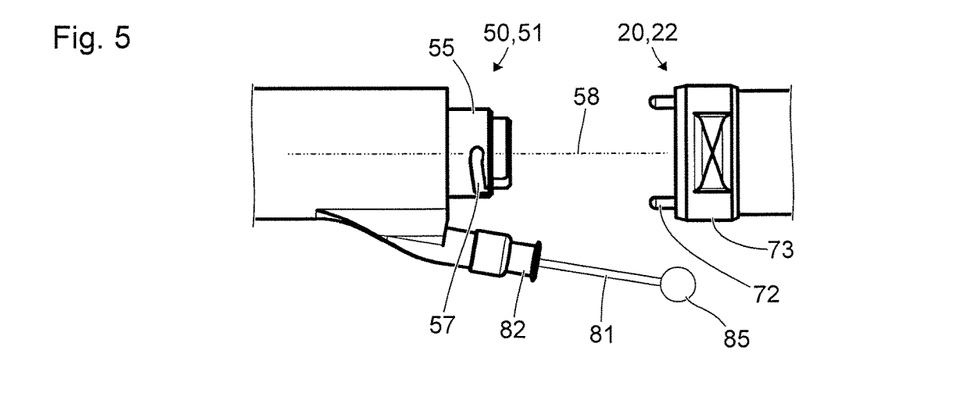
FIG. 5 shows a further schematic view of the distal end from FIG. 3 and of the proximal end from FIG. 4.

FIG. 5 shows a further schematic view of the distal end 22 of the maneuvering device 20 and of the proximal end 51 of the shaft 50 from FIGS. 1 to 4. The drawing plane of FIG. 5 is parallel to the drawing planes of FIGS. 1 and 2 and to the longitudinal axis 58. The distal end 22 of the maneuvering device 20 and the proximal end 51 of the shaft 50 are shown spaced apart from each other in a manner similar to FIG. 2. However, in contrast to FIG. 2, no features are shown that are not visible from the outside. Instead, in contrast to FIG. 3, the bolts 72 and the ring 73, which are described above with reference to FIG. 3, are shown in FIG. 5.

Figure 6:
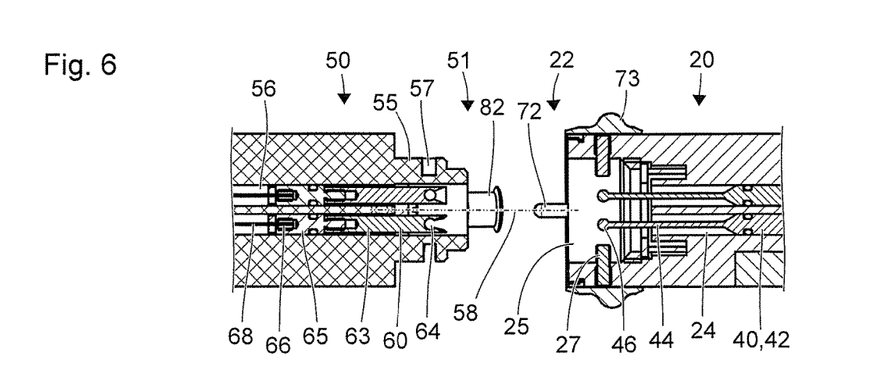
FIG. 6 shows a schematic sectional view of the distal end from FIGS. 3 and 5 and of the proximal end from FIGS. 4 and 5.

FIG. 6 shows a schematic sectional view of the distal end 22 of the maneuvering device 20 from FIGS. 3 and 5, and of the proximal end 51 of the shaft 50 from FIGS. 4 and 5. The sectional plane of FIG. 6 is perpendicular to the drawing planes of FIGS. 1, 2 and 5 and parallel to the longitudinal axis 58.

It will be seen from the cross section in FIG. 6 that the catches 27 are formed by pins which are inserted into the wall enclosing the recess 25. FIG. 6 also shows that the two transmission coupling devices 40 are arranged in two separate and parallel guide channels 24.

Moreover, FIG. 6 shows some features of the proximal end 51 of the shaft 50 that are not shown in FIGS. 1 to 5. In the proximal end 51 of the shaft 50, each transmission coupling device 60 is arranged and guided in a separate guide channel 56. Each transmission coupling device 60 at the proximal end 51 of the shaft 50 has, at its proximal end, a concave area or a recess 64 with a shape corresponding to the ball 46 at the distal end of a transmission coupling device at the distal end 22 of the maneuvering device 20. At the distal end, each transmission coupling device 60 has, in the proximal end 51 of the shaft 50, a mechanical connection 66 to an associated pull cable 68.

The cross sections of distal portions 65 of the transmission coupling devices 60 and of the guide channels 56 at the proximal end 51 of the shaft 50 are in particular circular. Proximal portions 63 of the transmission coupling devices 60 can each have a cross section of which the edge is composed of two mutually opposite arcs of a circle and two mutually opposite straight lines. In particular, each transmission coupling device is composed of a proximal portion 63 with the described non-circular cross section and of a distal portion 65 with a circular cross section, which portions are screwed onto each other for example.

Figure 7:
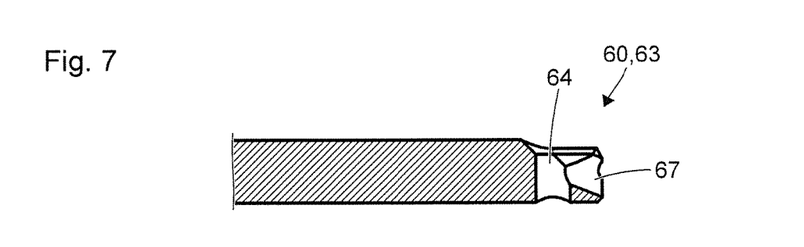
FIG. 7 shows a schematic view of a transmission coupling device.
Figure 8:
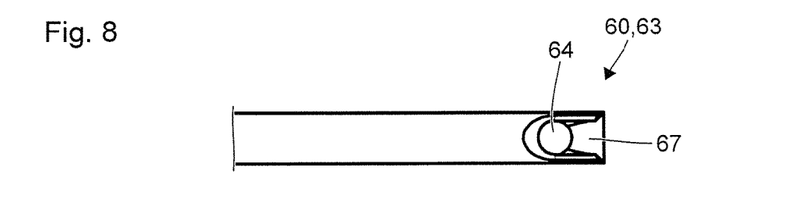
FIG. 8 shows a further schematic view of the transmission coupling device from FIG. 7.
Figure 9:
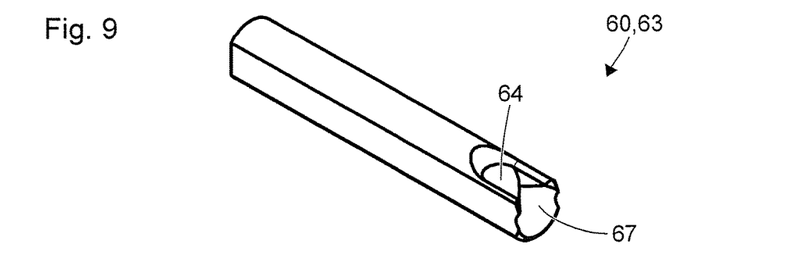
FIG. 9 shows a schematic axonometric view of the transmission coupling device from FIGS. 7 and 8.

FIGS. 7 to 9 show views of the proximal portion 63 of a transmission coupling device 60 at the proximal end 51 of a shaft 50 (cf. FIG. 6). FIG. 7 shows a schematic sectional view in which the sectional plane is parallel to the drawing planes of FIGS. 2 and 5, perpendicular to the drawing plane of FIG. 6 and parallel to the longitudinal axis 58. FIG. 8 shows a plan view in which the drawing plane is perpendicular to the drawing planes of FIGS. 2 and 5, parallel to the drawing plane of FIG. 6, and parallel to the longitudinal axis 58. FIG. 9 shows an axonometric view.

FIGS. 7 to 9 together show the shape of the proximal end of the proximal portion 63 of a transmission coupling device 60 at the proximal end 51 of the shaft 50 (cf. FIG. 6). The recess 64 is formed principally by a bore that has a circular cross section and that extends transversely with respect to the longitudinal axis 58 (cf. FIGS. 3 to 6). In the proximal direction from this bore, a substantially funnel-shaped area 67 is provided, of which the function and effect are explained below with reference to FIG. 12.

Figure 10:
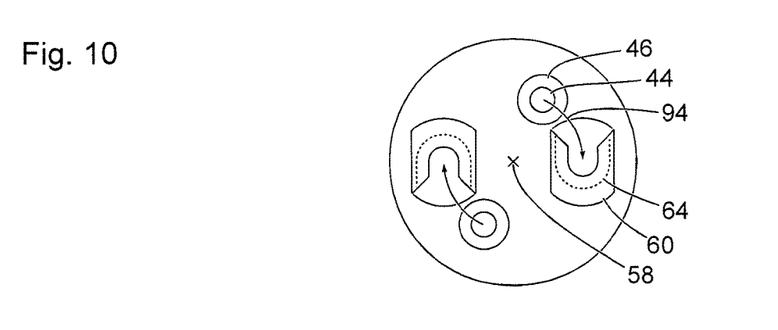
FIG. 10 shows a schematic view of a coupling procedure.
Figure 11:
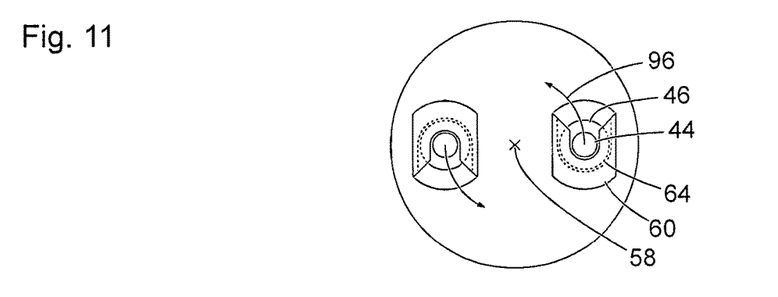
FIG. 11 shows a schematic view of an uncoupling procedure.

FIGS. 10 and 11 show schematic views of the balls 46 at the distal ends of the transmission coupling devices 40 in the maneuvering device 20 (cf. FIGS. 2, 3 and 6) and of the transmission coupling device 60 at the proximal end 51 of the shaft 50 (cf. FIGS. 4 and 6 to 9). The drawing planes of FIGS. 10 and 11 are perpendicular to the drawing planes of FIGS. 2 and 5 to 8 and perpendicular to the longitudinal axis 58.

FIG. 10 shows a situation or configuration in which the distal end 22 of the maneuvering device 20 and the proximal end 51 of the shaft 50 (cf. FIGS. 2 to 6) are brought fully together but are not mechanically connected to each other. In order to reach the configuration shown in FIG. 10, the catches 27 at the distal end 22 of the maneuvering device 20 (cf. FIG. 3) are moved through the axial portions as far as the circumferential portions, but not along the circumferential portions, of the L-shaped grooves 57 at the proximal end 51 of the shaft 50. The balls 46 at the distal ends of the transmission coupling devices 40 of the maneuvering device 20 are not yet arranged in the recesses 64 of the transmission coupling devices 60 at the proximal end 51 of the shaft 50.

Curved arrows 94 indicate a rotation movement of the maneuvering device 20 (cf. FIG. 2) together with the balls 46 at the distal ends of the transmission coupling devices 40 relative to the proximal end 51 of the shaft 50 and the transmission coupling devices 60 guided in the latter. During this rotation movement 94, the catches 27 at the distal end 22 of the maneuvering device 20 are moved in the circumferential portions of the L-shaped grooves 57. Moreover, the balls 46 can be moved into the recesses 64.

FIG. 11 shows a configuration in which the balls 46 at the distal ends of the transmission coupling devices 40 of the maneuvering device 20 are arranged in the recesses 64 of the transmission coupling devices 60 at the proximal end 51 of the shaft 50. In this way, a transmission coupling device 40 in the maneuvering device 20 and a transmission coupling device 60 at the proximal end 51 of the shaft 50 are mechanically coupled with a form fit: a movement of one transmission coupling device 40 of the maneuvering device 20 parallel to the longitudinal axis 58 is accompanied by a corresponding movement of the transmission coupling device 60 at the proximal end 51 of the shaft 50, and forces can be transmitted.

In the configuration shown in FIG. 11, the catches 27 at the distal end 22 of the maneuvering device 20 are arranged in the ends, remote from the axial portions, of the circumferential portions of the L-shaped grooves 57 at the proximal end 51 of the shaft 50. In this way, maneuvering device 20 and shaft 50 are mechanically rigidly connected to each other. In this configuration, the bolts 72 at the distal end 22 of the maneuvering device 20 (cf. FIGS. 3 and 5) can engage in the recesses 75 at the proximal end 51 of the shaft 50 (cf. FIG. 4) and lock the mechanical connection of maneuvering device 20 and shaft 50.

When the bolts 72 are moved in the proximal direction by means of the securing ring 73 (cf. FIG. 3; in particular counter to the force of springs or other elastic elements) and are thus withdrawn from the recesses 75 at the proximal end 51 of the shaft 50, the mechanical connection of shaft 50 and maneuvering device 20 is unlocked. In this unlocked state, a rotation movement indicated by arrows 96 in FIG. 11 can be performed by the maneuvering device 20, together with the balls 46 at the distal ends of the transmission coupling devices 40, relative to the proximal end 51 of the shaft 50. During this rotation movement 96, the balls 46 are moved out of the recesses 64 in the transmission coupling devices 60 at the proximal end 51 of the shaft 50. At the same time, the catches 27 at the distal end 22 of the maneuvering device 20 are moved through the circumferential portions as far as the axial portions of the L-shaped grooves 57 at the proximal end 51 of the shaft 50 (cf. FIGS. 3 to 5). In this way, the mechanical coupling between the mechanical transmission coupling devices 40, 60 of the maneuvering device 20 and of the shaft 50 is separated. Thereafter, the maneuvering device 20 and the proximal end 51 of the shaft 50 can be separated from each other by a relative movement parallel to the longitudinal axis 58. The catches 27 at the distal end 22 of the maneuvering device 20 are moved through the axial portions of the L-shaped grooves 57 at the proximal end 51 of the shaft 50.

Each transmission coupling device 40 of the maneuvering device 20 is movable parallel to the longitudinal axis 58 independently of the associated transmission coupling device 60 at the proximal end 51 of the shaft 50. However, it is only in a relative positioning of both transmission coupling devices 40, 60 that the ball 46 at the distal end of the transmission coupling device 40 of the maneuvering device 20 can be received directly in the recess 64 at the proximal end of the transmission coupling device 60 of the shaft 50, as is indicated in FIG. 10 by the arrows 94. However, as is described in more detail below with reference to FIG. 12, a complete run through all the possible positions of the balls 46 (in particular by actuation of the actuating device 30—cf. FIG. 2) is sufficient to cause the balls 46 to be received in the recesses 64 and thereby to effect a mechanical coupling of the respectively associated transmission coupling devices 40, 60.

Figure 12:
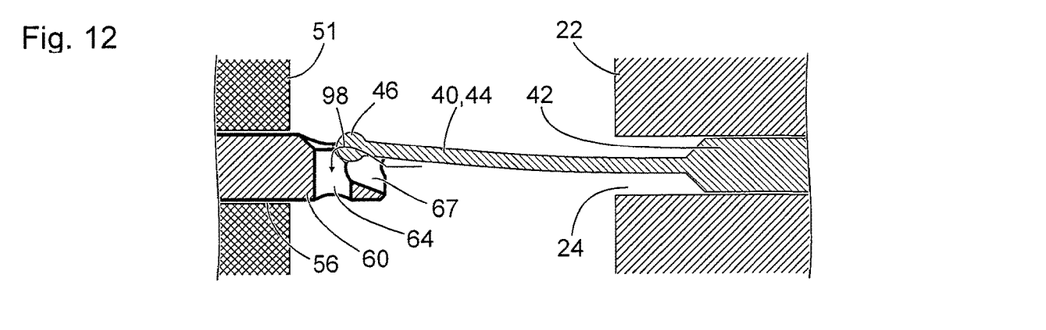
FIG. 12 shows a schematic view of a further coupling procedure.

FIG. 12 shows a schematic sectional view of a transmission coupling device 40 in a guide channel 24 of the maneuvering device 20, and of the associated transmission coupling device 60 in the guide channel 56 at the proximal end 51 of the shaft 50. The sectional plane of FIG. 12 is parallel to the drawing planes of FIGS. 1, 2, 5 and 7, perpendicular to the drawing planes of FIGS. 6, 8, 10 and 11, and parallel to the longitudinal axis 58. An arrow 98 indicates a movement which starts from a position of the ball 46 in the proximal direction from the proximal end of the transmission coupling device 60 of the shaft 50, and in which the transmission coupling device 40 of the maneuvering device 20 is moved in the distal direction relative to the transmission coupling device 60 of the shaft 50. The funnel-like area 67, described above with reference to FIGS. 7 to 9, acts like a ramp or a wedge and so deflects the ball 46 perpendicularly with respect to the longitudinal axis 58 as far as the position shown in FIG. 12, in which the elastic portion 44 of the transmission coupling device 40 of the maneuvering device 20 is elastically deformed. When, starting from the position shown in FIG. 12, the transmission coupling device 40 of the maneuvering device 20 is moved further in the distal direction relative to the transmission coupling device 60 of the shaft 50, the ball 46 enters the recess 64, as is indicated by the arrow 98. This position (not shown) results in the mechanical coupling, also described above with reference to FIG. 11, of the associated transmission coupling devices 40, 60.

REFERENCE SIGNS 10 medical instrument
11 proximal end of the medical instrument 10
12 distal end of the medical instrument 10
14 tool at the distal end 12 of the medical instrument 10
20 maneuvering device
22 distal end of the maneuvering device 20

23 movable grip part
24 guide channel for transmission coupling device 40 in the maneuvering device 20
25 recess at the distal end 22 of the maneuvering device 20
27 catch on the maneuvering device 20
30 actuating device on the maneuvering device 20
32 crank rigidly connected to the actuating device 30
34 connector rod between crank 32 and first transmission coupling device 40
38 pivot axis of the actuating device 30
40 transmission coupling device on the maneuvering device 20
42 portion of the transmission coupling device 40 guided in the guide channel 24
44 elastic portion on the transmission coupling device 40
46 ball at the distal end of the transmission coupling device 40
50 shaft of the medical instrument 10
51 proximal end of the shaft 50
52 distal end of the shaft 50
53 uncontrolled flexible portion of the shaft 50
54 controlled curvable portion of the shaft 50
55 convex area at the proximal end 51 of the shaft 50
56 guide channel for transmission coupling device 60 in the proximal end 51 of the shaft 50
57 L-shaped groove at the proximal end 51 of the shaft 50 for the catch 27 on the maneuvering device 20
58 longitudinal axis of the proximal end 51 of the shaft 50
59 recess at the proximal end 51 of the shaft 50 for bolt 72 on the maneuvering device 20
60 transmission coupling device at the proximal end 51 of the shaft 50
63 proximal portion of the transmission coupling device 60
64 recess on the transmission coupling device 60 corresponding to the ball 46
65 distal portion of the transmission coupling device 60
66 mechanical connection of the transmission coupling device 60 to the pull cable 68
67 funnel-like area at the proximal portion 63 of the transmission coupling device 60
68 pull cable in the shaft 50 for controlling the controlled flexible portion 54
72 bolt on the maneuvering device 20
73 ring on the maneuvering device 20
75 recess at the proximal end 51 of the shaft 50 for bolt 72 on the maneuvering device 20
81 further transmission device
82 nozzle
85 further transmission coupling device
94 rotation movement for connection
96 rotation movement for separation
98 coupling of the relative movement of the transmission coupling devices 40, 60

The invention claimed is:

1. A shaft for a medical instrument, comprising:
a tool or a coupling for a tool;
a controlled curvable portion or a hinge;
an uncontrolled flexible portion;
a shaft coupling device configured to releasably mechanically connect the shaft to a maneuvering device;
a transmission device configured to transmit at least one of a force and a torque between a proximal end of the shaft and the controlled curvable portion or the hinge;
a transmission coupling device at the proximal end of the shaft, the transmission coupling device configured to releasably mechanically couple to a ball at a distal end of a corresponding transmission coupling device in the maneuvering device, a proximal portion of the transmission coupling device having a funnel-shaped area configured to deflect the ball in a direction perpendicular to a longitudinal axis of the transmission device as the ball is moved relative to the funnel-shaped area in a direction parallel to the longitudinal axis of the transmission device during releasable mechanical coupling of the transmission coupling device to the ball.

2. The shaft according to claim 1, wherein the transmission device includes a pull cable or a pull wire.

3. The shaft according to claim 1, wherein the transmission coupling device at the proximal end of the shaft provides a latching connection to the corresponding transmission coupling device in the maneuvering device.

4. The shaft according to claim 1, wherein the transmission coupling device at the proximal end of the shaft has, at its proximal end, a concave portion.

5. The shaft according to claim 1, wherein the shaft coupling device and the transmission coupling device at the proximal end of the shaft are configured such that a mechanical connection between the shaft coupling device and a corresponding coupling device of the maneuvering device and a mechanical coupling of the transmission coupling device to the corresponding transmission coupling device in the maneuvering device are releasable by rotating the shaft about a longitudinal axis of the shaft and relative to the maneuvering device.

6. The shaft according to claim 5, wherein the transmission device includes a pull cable or a pull wire.

7. The shaft according to claim 5, wherein the transmission coupling device at the proximal end of the shaft provides a latching connection to the corresponding transmission coupling device in the maneuvering device.

8. The shaft according to claim 5, wherein the transmission coupling device at the proximal end of the shaft has, at its proximal end, a concave portion.

9. The shaft according to claim 5, wherein the transmission coupling device at the proximal end of the shaft includes several transmission coupling devices, wherein the several transmission coupling devices are configured to control the controlled curvable portion or hinge.

10. The shaft according to claim 5, further comprising:
a further transmission device configured to transmit at least one of a force and a torque between a proximal end of the shaft and the tool disposed at a distal end of the shaft; and
a further transmission coupling device mechanically coupling the further transmission device to a corresponding further transmission coupling device on the maneuvering device;
wherein the further transmission device is arranged outside the shaft coupling device.

11. The shaft according to claim 1, wherein the transmission coupling device at the proximal end of the shaft includes several transmission coupling devices, wherein the several transmission coupling devices are configured to control the controlled curvable portion or hinge.

12. The shaft according to claim 11, wherein the several transmission coupling devices are arranged symmetrically with respect to a longitudinal axis of the shaft.

13. The shaft according to claim 1, further comprising:
a further transmission device configured to transmit at least one of a force and a torque between a proximal end of the shaft and the tool disposed at a distal end of the shaft; and a further transmission coupling device mechanically coupling the further transmission device to a corresponding further transmission coupling device on the maneuvering device;

wherein the further transmission device is arranged outside the shaft coupling device.

14. A medical instrument, comprising:
a shaft having:
   a tool or a coupling for a tool;
   a controlled curvable portion or a hinge; and
   an uncontrolled flexible portion;
a maneuvering device having an actuating device configured to control the tool or the coupling for the tool, the actuating device having a ball at a distal end thereof;
a shaft coupling device configured to releasably mechanically connect the shaft to the maneuvering device; and
a transmission device configured to transmit at least one of a force and a torque between a proximal end of the shaft and the controlled curvable portion or the hinge;
a transmission coupling device disposed at the proximal end of the transmission device, the transmission coupling device configured to releasably mechanically couple to the ball at the distal end of the actuating device of the maneuvering device, a proximal portion of the transmission coupling device having a funnel-shaped area configured to deflect the ball in a direction perpendicular to a longitudinal axis of the transmission device as the ball is moved relative to the funnel-shaped area in a direction parallel to the longitudinal axis of the transmission device during releasable mechanical coupling of the transmission coupling device to the ball.

15. The medical instrument of claim 14, wherein the transmission device includes a pull cable or a pull wire.

16. The medical instrument of claim 14, wherein the transmission coupling device at the proximal end of the shaft provides a latching connection to the ball at the distal end of the actuating device of the maneuvering device.

17. The medical instrument of claim 14, wherein the transmission coupling device at the proximal end of the shaft has, at its proximal end, a concave portion.

18. The medical instrument of claim 14, wherein the transmission coupling device at the proximal end of the shaft includes several transmission coupling devices, wherein the several transmission coupling devices are configured to control the controlled curvable portion or hinge.

19. The medical instrument of claim 18, wherein the several transmission coupling devices are arranged symmetrically with respect to a longitudinal axis of the shaft.

20. The medical instrument of claim 14, further comprising:
   a further transmission device configured to transmit at least one of a force and a torque between a proximal end of the shaft and the tool disposed at a distal end of the shaft; and
   a further transmission coupling device mechanically coupling the further transmission device to a corresponding further transmission coupling device on the maneuvering device;
   wherein the further transmission device is arranged outside the shaft coupling device.

21. The medical instrument of claim 14, wherein the shaft coupling device and the transmission coupling device at the proximal end of the shaft are configured such that a mechanical connection between the shaft coupling device and a corresponding coupling device of the maneuvering device and a mechanical coupling of the transmission coupling device to the ball in the maneuvering device are releasable by rotating the shaft about a longitudinal axis of the shaft and relative to the maneuvering device.

* * * * *